United States Patent
Duran et al.

(10) Patent No.: US 7,125,418 B2
(45) Date of Patent: Oct. 24, 2006

(54) SIGMOID VALVE AND METHOD FOR ITS PERCUTANEOUS IMPLANTATION

(75) Inventors: Carlos Duran, Missoula, MT (US); Mark Sanz, Missoula, MT (US)

(73) Assignee: The International Heart Institute of Montana Foundation, Missoula, MT (US)

( * ) Notice: Subject to any disclaimer, the term of this patent is extended or adjusted under 35 U.S.C. 154(b) by 133 days.

(21) Appl. No.: 10/411,797

(22) Filed: Apr. 11, 2003

(65) Prior Publication Data

US 2004/0215333 A1 Oct. 28, 2004

Related U.S. Application Data

(60) Provisional application No. 60/373,171, filed on Apr. 16, 2002.

(51) Int. Cl.
  *A61F 2/06* (2006.01)
(52) U.S. Cl. ..................................... 623/1.24
(58) Field of Classification Search ............... 623/1.24, 623/1.26, 2.12, 2.13
  See application file for complete search history.

(56) References Cited

U.S. PATENT DOCUMENTS

| | | | |
|---|---|---|---|
| 5,957,949 A * | 9/1999 | Leonhardt et al. | 623/1.24 |
| 6,277,555 B1 | 8/2001 | Duran et al. | |
| 6,299,637 B1 * | 10/2001 | Shaolian et al. | 623/1.24 |
| 6,352,708 B1 | 3/2002 | Duran et al. | |
| 6,425,916 B1 * | 7/2002 | Garrison et al. | 623/2.11 |
| 6,458,153 B1 * | 10/2002 | Bailey et al. | 623/1.24 |
| 6,494,909 B1 * | 12/2002 | Greenhalgh | 623/1.24 |
| 6,685,739 B1 * | 2/2004 | DiMatteo et al. | 623/1.24 |
| 6,733,525 B1 * | 5/2004 | Yang et al. | 623/2.18 |
| 2003/0209835 A1 * | 11/2003 | Chun et al. | 264/339 |
| 2005/0075713 A1 * | 4/2005 | Biancucci et al. | 623/1.11 |

OTHER PUBLICATIONS

Bonhoeffer et al. Transcatheter Implantation of a Bovine Valve in Pulmonary Position: A Lamb Study. *Circulation* 2000;102:813-816.
Bonhoeffer et al. Percutaneous replacement of pulmonary valve in a right-ventricle to pulmonary-artery prosthetic conduit with valve dysfunction. *The Lancet* 2000; 356; 1403-1405.
Cribier et al. Percutaneous Transcatheter Implantation of an Aortic Valve Prosthesis for Calcific Aortic Stenosis: First Human Case Description. *Circulation* 2002; 106; 3006-3008.

* cited by examiner

*Primary Examiner*—Alvin J. Stewart
(74) *Attorney, Agent, or Firm*—Gabor L. Szekeres (57) ABSTRACT

A multi-leaflet valve adapted to serve as a prosthesis for diseased native valve of a mammal is incorporated in self-expandable or inflatable endovascular stents or stents to form a combination which is introduced on a catheter with a guide wire into the circulatory system of the mammal to replace the diseased native valve. Once the combination is at the desired location the stent is caused to expand and affix itself to the patient's vessel wall. The prosthetic valve has the shape of a truncated cone that has an inflow and an outflow orifice with leaflets forming the outflow orifice and forming a plurality of commissures. A first flexible circular support is affixed in a substantially circular fashion around the truncated cone in proximity of the inflow orifice, and a second flexible circular support is affixed at the location of the commissures to form a circle around the truncated cone in proximity of the outflow orifice. The circular supports maintain the shape of the valve during the surgical implantation procedure and thereafter.

8 Claims, 5 Drawing Sheets

SIGMOID VALVE AND METHOD FOR ITS PERCUTANEOUS IMPLANTATION

CROSS-REFERENCE TO PRIORITY APPLICATION

The present application claims the priority of provisional application Ser. No. 60/373,171 filed on Apr. 16, 2002.

BACKGROUND OF THE INVENTION

1. Field of the Invention

The present invention is in the field of one-way valves designed to replace diseased venous or arterial valves present in the circulatory system. More specifically, the present invention is directed to the replacement of a diseased valve in the circulatory system through a percutaneous approach.

2. Description of Background Art

The Sigmoid Valves

The mammalian circulation needs the presence of one-way valves to maintain forward blood flow. These valves are found in the outflow of the right and left ventricles ("pulmonary" and "aortic" valves, respectively), and in the large veins. Because of their similar anatomic structure, they are called "sigmoid" or "semilunar" valves. This common structure consists of one, two, or three very thin flaps called "cusps" or "leaflets." Each flap has a semicircular shape with a curved free edge and a curved base that is inserted into the vessel wall. The insertion of the free edge of the cusp to the vessel wall is called the "commissure." Immediately downstream to each leaflet, the wall of the vessel has three dilatations or bulges called "sinuses of Valsalva." There are as many sinuses of Valsalva as leaflets (i.e., a trileaflet valve has three sinuses). These elements of the normal sigmoid have been incorporated in the design of the present invention.

Sigmoid Valve Replacement

In disease, the function of the sigmoid valves is impaired either through narrowing of the valve ("stenosis") or lack of complete closure, which results in backflow ("regurgitation"). In both circumstances, the whole circulation of the blood and the heart is altered and causes severe symptoms in the patient. Although replacement of the diseased cardiac valves is frequently performed with prostheses, replacement of the venous valves is not done because of the lack of an appropriate prosthesis. According to the material used, heart valve prostheses are classified as mechanical or biologic. Mechanical valves do not resemble the natural sigmoid valves. The biologic prostheses replicate natural anatomy. Tissue valves can be normal sigmoid valves obtained from a cadaver (homograft) or animal (xenograft). Most xenografts are tanned with glutaraldehyde to reduce rejection and increase durability. These hybrids, called "bioprostheses," are presently the most popular tissue valves. More recently, to improve their hemodynamic performance, tanned animal sigmoid valves have been implanted without a stent (stentless bioprosthesis).

The surgical implantation of heart valve prostheses is a major operation that requires opening the chest and going on cardiopulmonary bypass. The success of percutaneous vascular stenting in coronary and peripheral arteries has encouraged attempts at placing a biologic valve within a large supporting stent so that it can be delivered through a catheter and deployed in the desired position. Recently, two sigmoid valves have been percutaneously implanted in patients. The publications by Bonhoeffer et al. Implantation of a Bovine Valve in Pulmonary Position: A Lamb Study. *Circulation* 2000;102:813–816 and Bonhoeffer et al. Percutaneous replacement of pulmonary valve in a right-ventricle to pulmonary-artery prosthetic conduit with valve dysfunction. *Lancet* 2000;356:1403–1405 describe successful percutaneous implantation of a glutaraldehyde-treated bovine jugular valve placed within a stent and deployed inside a previously implanted valved conduit in the pulmonary position. The publication by Cribier et al. Percutaneous Transcatheter Implantation of an Aortic Valve Prosthesis for Calcific Aortic Stenosis. First Human Case Description. *Circulation* 2002;106:3006–3008 describes aortic valve replacement with a valve made of three bovine pericardial leaflets mounted within a tubular, slotted, stainless steel balloon-expandable stent.

SUMMARY OF THE INVENTION

The present invention is a novel system designed to provide a sigmoid tissue valve that can be implanted percutaneously to replace a diseased valve primarily within the circulatory system, although its placement in other body channels is also possible. The system comprises three basic elements: a flexible, biologic tissue sigmoid valve; a flexible supporting stent that holds the sigmoid valve and that can be collapsed and expanded; and a catheter-based delivery system to deploy the device in the desired location of the mammalian, including human, body.

DETAILED DESCRIPTION OF THE INVENTION

The following specification, taken in conjunction with the drawings, sets forth the preferred embodiments of the present invention. The embodiments of the invention disclosed herein are the best modes contemplated by the inventors for carrying out their invention in a commercial environment, although it should be understood that various modifications can be accomplished within the parameters of the present invention.

GENERAL DESCRIPTION

The Valve

It should be noted at the outset that the valve of the present invention can have one, two, or three leaflets. Nevertheless, the preferred embodiment is a trileaflet sigmoid valve and for this reason, the ensuing description refers to a trileaflet valve.

Thus, the tricuspid (or bicuspid) valve of the invention (see for example FIG. 6) can be made of a flexible, flat membrane of biocompatible synthetic or biologic material of autologous, homologous, or heterologous tissue, such as pericardium, pleura, peritoneum, or dura mater. The membrane is placed on a template of the appropriate size and shape (see FIGS. 3 and 4). The material is trimmed to acquire a trapezoidal shape of the desired form. The trimmed membrane has such a shape that when its lateral aspects are joined together (see FIG. 6), a truncated cone is formed with a base (or inflow) orifice slightly larger than its distal (or outflow) orifice. The inflow orifice is cut into a single plane and the outflow orifice is trimmed into two or three curvatures corresponding to the free edges of the new bi-leaflet or tri-leaflet prosthesis. The points where the free edge curvatures are in continuity correspond to the two or three commissures of the new prosthesis. The height of the membrane at the level of the three commissures corresponds to the distance between the base of a normal sigmoid valve and its commissures, adding a few millimeters to increase the area of coaptation of the new leaflets.

Alternatively, the valve of the invention can be made of an already existing conduit of synthetic or biologic origin (such as artery or vein) or other tubular body channel (such as gut, lymphatic vessel, or ureter) of autologous, homologous, or heterologous origin. A conduit of the desired length and diameter is selected. Its length must correspond to the calculated distance between the base and the top of the commissures of the natural sigmoid valve, adding a few millimeters to ensure good leaflet coaptation. One extremity of the conduit is sectioned perpendicular to the direction of the conduit. This end will constitute the inflow orifice. The other end of the conduit, or outflow orifice of the prosthesis, is trimmed according to whether a bi-leaflet or tri-leaflet valve is constructed. The membrane is trimmed so that two or three equidistant curvatures result, corresponding to the free edges of the two or three new leaflets. The point where the curvatures meet corresponds to the valve commissures. Although the inflow orifice of the sigmoid valve is completely attached to the endovascular stent, the outflow orifice of the sigmoid valve is only attached to the endovascular stent at three points, corresponding to the commissures of the sigmoid valve.

As another alternative, the valve of the invention is constructed of a natural, biologic sigmoid valve, such as the pulmonary, aortic, or vein roots of autologous, homologous, or heterologous origin. The sigmoid valve is dissected, removing as much as possible of the vessel wall so that a minimum of nonleaflet tissue is left. The inflow orifice is then formed by a narrow, horizontal band of cardiac muscle, fibrous tissue, or vessel (according to the origin of the tissue). This inflow orifice is attached to the supporting stent along its circumference. The scalloped outflow orifice is attached to supporting stent at only three points, corresponding to the three commissural points of the valve.

The inflow and outflow orifices of the sigmoid valve are supported with one suture that is threaded through the base of the inflow orifice and another suture that holds the three equidistant commissural stitches in position. These sutures are designed to facilitate the correct positioning and anchoring of the sigmoid valve within an endovascular stent. These sutures are hereinafter called first, or inflow, and second, or outflow, encircling support; the first one is located at the inflow orifice, and the second one is attached to the three commissures.

Figures 11A, 11B:
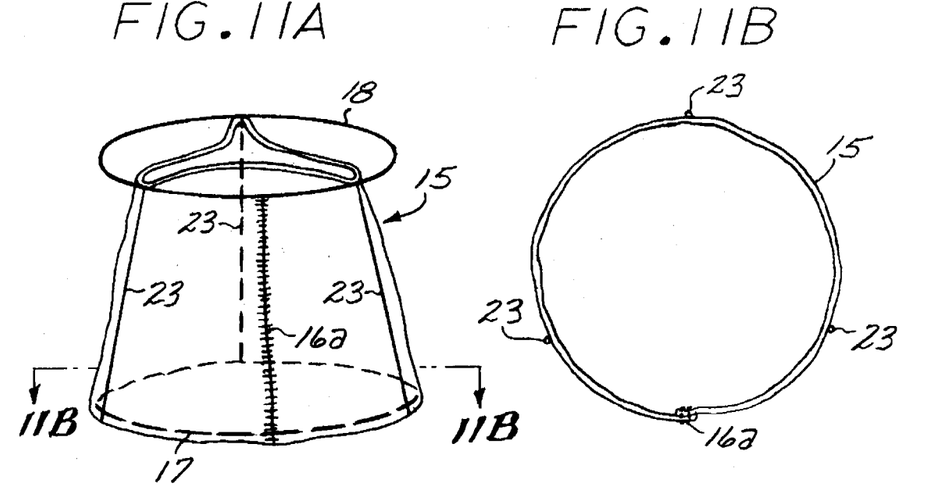
FIG. 11A is a schematic perspective view of the valve of the present invention that is to be included in the systems of FIGS. 7A, 7B and 8A, 8B, and 8C.
FIG. 11B is a cross-sectional view taken on lines 11B of FIG. 11A.

As a further alternative, three flexible wires or sutures are fixed between the inflow and outflow orifices of the sigmoid valve of the present invention at the level corresponding to the valve commissures (for such valve per se see FIGS. 11A and 11B).

Tissue Treatment

The manufacturing process of the device of the present invention requires a number of steps that are delicate and time consuming. In accordance with the present invention, the valve is preferably manufactured in a commercial environment where all the steps are performed by dedicated personnel who dissect the tissue and construct the valve. The valve is treated with a variety of chemical stabilizing solutions, such as glutaraldehyde, or preferably with a non-glutaraldehyde process described in U.S. Pat. No. 6,277,555 B1 and then anchored to a variety of endovascular stent systems here described. Alternatively, the valve is anchored first followed by the chemical treatment. The chemically treated sigmoid valve placed within the endovascular stent system is then collapsed within a delivery catheter system. The valve, stent and delivery system (to the extent the delivery system parts are present) is then subjected to a freeze-drying process described in U.S. Pat. No. 6,352,708 B1, and packaged. The final product is also gas or electron beam sterilized in the dry state. The specifications of U.S. Pat. Nos. 6,277,555 B1 and 6,352,708 B1 are expressly incorporated herein.

The delivery catheter system per se is well known in the art. It consists of a guide wire that is introduced percutaneously and placed in the desired position of the vessel or heart. The guide wire runs within the delivery catheter. The delivery catheter carries the valve and endovascular stent in a collapsed status. After they are correctly positioned, the valve and stent are expanded by either inflating a balloon or using a stent made of an alloy that has memory. Once delivered, it expands spontaneously to the desired size. The delivery catheter and guide wire are then removed from the patient.

The Valve Supporting Mechanism

A specific and permanent system to attach the sigmoid valve of the present invention to the vessel wall of the patient in combination with the valve is an aspect of the invention. The collapsible sigmoid valve must be attached to a collapsible valve support system or device that is inserted within a delivery catheter through a peripheral vessel, such as the femoral vessels, carotid artery, or jugular vein. The device or system, including the sigmoid valve and support system, is self expandable or balloon expandable to fix it into the desired location of the circulatory system. Although the apparent locations are the subcoronary position of the aortic valve, ascending and descending aorta, pulmonary valve, pulmonary trunk, right ventricular outflow tract, and large peripheral veins, the device or system of the present invention can be used in any other channel of the body that might require the presence of a valve within or outside the circulation. The present invention includes several and various means for ensuring the anchoring of the sigmoid valve of the present invention to the patient's vessel wall.

Figure 7:
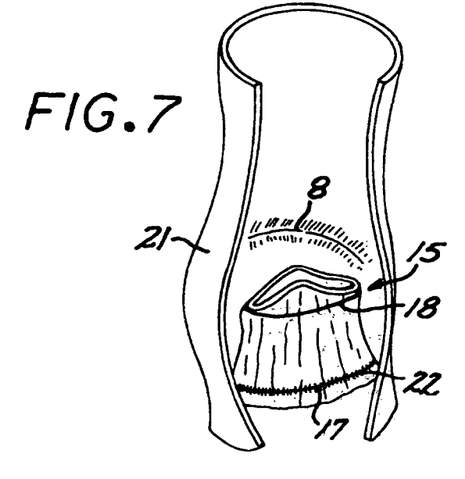
FIG. 7A is a schematic perspective view of the valve of the present invention placed within a straight endovascular stent.
FIG. 7B is a schematic perspective view of the valve within the endovascular stent after the inflow and outflow circular supports of the valve have been sutured to the endovascular stent, resulting in a bulge or sinus of Valsalva.
Figure 7A:
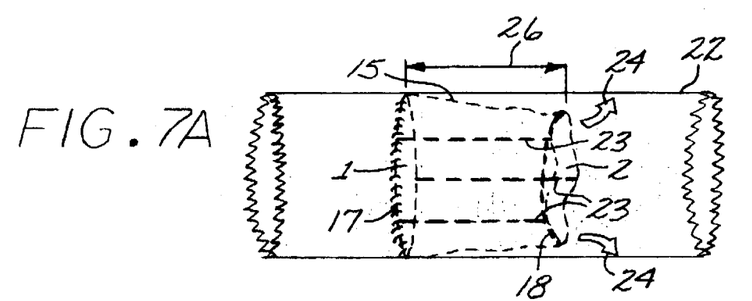

In one embodiment, the sigmoid valve is placed within a collapsible tubular endovascular stent longer than the overall length of the sigmoid valve (see FIG. 7A). This tubular endovascular stent can have a cylindrical or truncated cone configuration. After it has been introduced into the proper location in the circulatory system of the patient, the endovascular stent self-expands or is expanded by balloon and fixes itself to the vessel wall. In this embodiment, the intravascular stent is made of tubular mesh that is not in contact with the aortic wall at the level of the sinuses of Valsalva of the patient, but the endovascular stent lies within the sinuses of Valsalva exposed to the blood flow. Whereas this device and manner of implantation is workable, it poses some danger of thrombosis.

Figure 7B:
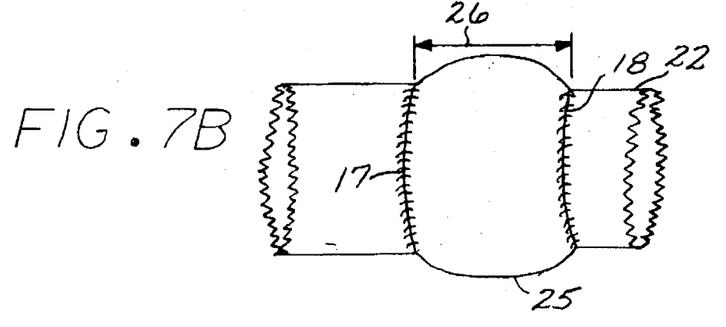

An alternative embodiment is shown in FIG. 7B. Although the stent mesh is a straight tube, the anchoring of the distal orifice of the sigmoid valve is sutured to a point of the stent longer than the height of the valve. This disparity between the shorter height of the valve and the length of the stent will determine that the stent will bulge out. Given that the endovascular stent is made of a metal open mesh, it can be deformed and expanded differentially. This is shown in FIGS. 7A and 7B. In FIG. 7A, the valve is placed within a straight stent. In FIG. 7B, although the valve is placed within a straight stent, the arrows try to show that its outflow orifice is sutured to the ring beyond its natural length and therefore, the stent has to bulge out.

Figure 8:
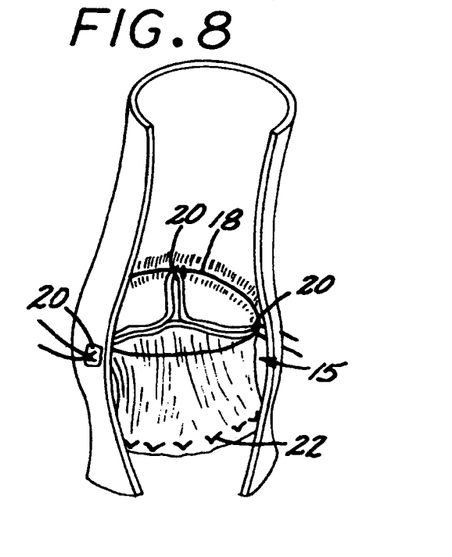
FIG. 8A is a schematic perspective view of the valve of the present invention placed within an endovascular stent constructed with a dilatation or bulge.
FIG. 8B is an end view of the inflow orifice of the open sigmoid valve sutured to the endovascular stent of FIG. 8A.
FIG. 8C is an end view of the outflow orifice of the closed sigmoid valve sutured to the endovascular stent of FIG. 8A.
Figure 8A:
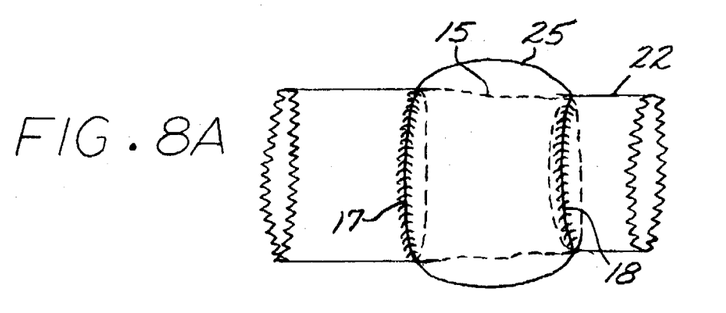
Figure 8B:
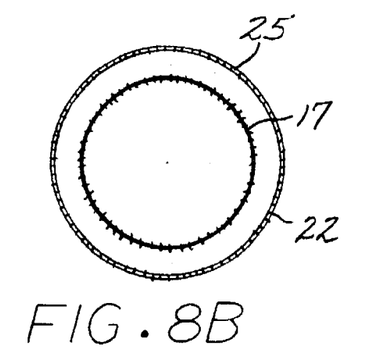
Figure 8C:
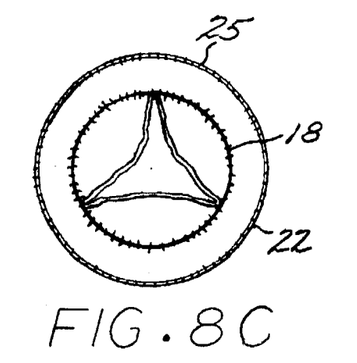

In another embodiment of the valve support system (see FIG. 8), the midportion of the tubular endovascular stent has a concentric expansion with a diameter larger that the extremities of the tubular stent so that the tubular stent is in direct contact with the vessel wall at the level of the sinuses of Valsalva.

In still another embodiment (not shown), the midportion of the self-expanding stent is expanded into three bulges corresponding to the configuration of the sinuses of Valsalva present in normal sigmoid valves. This is achieved by manufacturing an endovascular stent with an alloy that has memory (e.g., NITINOL™) so that it acquires the desired shape after it is implanted and released.

Figure 9:
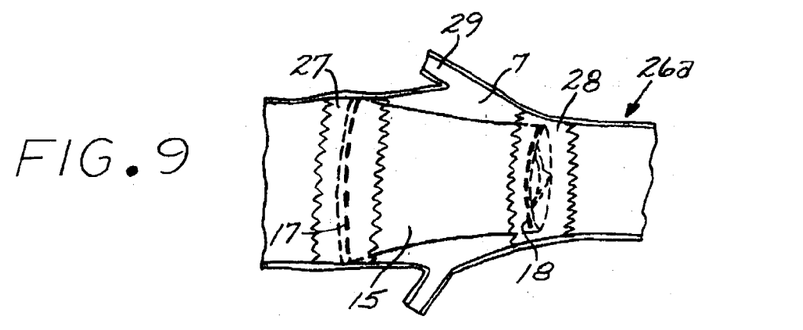
FIG. 9 is schematic perspective view of the valve of the invention within a patient's vessel and held by two separate endovascular stents.

As still another alternative, the inflow and outflow orifices of the sigmoid valve and the first and second encircling supports are sutured to two independent, short collapsible stents (see FIG. 9). After implantation, when both stents are expanded, they anchor the inflow and outflow extremities of the sigmoid valve to the vessel wall below and above the sinuses of Valsalva of the patient. Because the sigmoid valve is only anchored at its extremities, the proximal and distal endovascular stents and first and second encircling supports do not interfere with the coronary orifices. In the prior art, interference with the coronary orifices is one of the main problems of percutaneous implantation of an aortic valve.

The inflow orifice of the valve shown in FIGS. 11A and 11B is sutured within a flexible, straight endovascular metal or plastic stent of the type shown in FIG. 7A. In this embodiment, the outflow orifice (i.e., the three valve commissures) is attached to the endovascular stent at a point further than its length so that the flexible endovascular stent is compressed and dilates, imitating the sinuses of Valsalva. These collapsible metal or plastic endovascular stents are well known in the art and are commercially available. The metal or plastic endovascular stent can be made of stainless steel mesh, metal alloys, or plastics. If the material has memory, it will expand spontaneously after it is freed from its delivery catheter. If the metal or plastic stent does not expand spontaneously, a balloon is incorporated that can be inflated to expand the stent to its predetermined size.

In still another alternative embodiment (see FIG. 10), a short segment of a vascular conduit of the appropriate diameter is sutured to the inflow and outflow orifices of the sigmoid valve of the present invention. These vascular conduits can be made of commercially available synthetic fabric or of biologic tissue. A series of small metal or plastic hooks are attached to both extremities of the conduit. Balloon expansion of the vascular conduit carrying the metal hooks anchors both vascular conduits to the vessel wall of the patient. This system is well known in the art and is particularly applied clinically for the treatment of aortic aneurysms.

Percutaneous Implantation

The flexible sigmoid valve and supporting flexible mechanism of the present invention are collapsed and plicated for placement within a delivery catheter system. The term "plicated" means collapsed and rolled (or wrapped) to reduce its diameter, which makes it possible to place it within a delivery catheter system.

The characteristics of the sigmoid valve of the present invention are especially designed for its percutaneous implantation. Although the inflow orifice of the valve is fully attached to the different types of supporting endovascular stents described above, the outflow orifice is attached only to the endovascular stent at the three commissures, resulting in a single open space between the sinuses of Valsalva. This configuration solves one of the major problems of the percutaneous implantation of a sigmoid valve to replace the aortic valve. When a conventional tissue valve is attached to the stent, the inflow orifice of the valve is fixed along its whole circumference. The outflow orifice needs to be sutured to the endovascular stent along its whole scalloped wall of the valve. In fact, this technique is the standard method to surgically implant a stentless tissue valve. Care must be taken to orient the valve so that the commissures of the tissue valve correspond with the patient's commissures. Small degrees of malrotation of the valve can result in obstruction of the coronary orifices (with untoward serious consequences). In the present invention, because of the free space between the top of the commissures and the inflow suture, orientation of the valve is not critical.

Delivery System

Several systems known in the art are available for the percutaneous delivery of endovascular arterial and venous stents, coils, umbrellas, filters, and occluding devices. In the case of catheter delivery systems of a sigmoid valve and its supporting mechanism, a balloon catheter with a central orifice for the passage of a guide wire well known in the art is passed through the sigmoid valve and the anchoring system. The deflated balloon, together with the sigmoid valve and its endovascular support system, is collapsed and rolled around the balloon catheter and introduced into a delivery catheter. The delivery catheter is introduced percutaneously and directed by the guide wire. Alternatively, the valve-supporting endovascular stent can be self-expandable so that after it is delivered from its deploying catheter, the stent expands spontaneously in the desired locatio The primary novel feature of the present invention is in the completely original sigmoid valve. Previous attempts at delivering a tissue valve percutaneously have used a porcine or pericardial valve within a large single stent. In the prior art, the tissue valve used is dissected or manufactured as a conduit containing three leaflets. The conduit is placed within the stent and held with two circular sutures corresponding to the inflow and outflow orifices. A good example of this technique is described in Bonhoeffer et al. Implantation of a bovine valve in pulmonary position: A lamb study. *Circulation* 2000;102:813–816 and Bonhoeffer et al. Percutaneous replacement of pulmonary valve in a right-ventricle to pulmonary-artery prosthetic conduit with valve dysfunction. *Lancet* 2000;356:1403–1405, where a trileaflet valve made from bovine jugular vein is placed into an 18 mm intravascular stent. In this prior art device, the tubular portion of the jugular vein spanned the entire length of the stent. Although a successful clinical case of such a device placed percutaneously in the pulmonary position has been recently reported, this technique has several disadvantages.

First, the valve is relatively stenotic, because a complete valve root is used within the stent. Aortic and pulmonary roots have a thick myocardial base and thick vessel wall. No matter how much care is taken to trim down these tissues, a significant amount of tissue remains. Although the jugular vein valve does not have a myocardial cuff in its base, it is not free from this problem, as recognized in the publication *Circulation* 2000;102:813–816. Referring to results obtained in seven experimental sheep, the postoperative mean systolic transvalvular gradients were 18 mm Hg immediately after implantation and 15 mm Hg two months later despite having trimmed the wall of the vein.

Second, because the whole root of the biologic valve is used as a tube, this prior art method cannot be used in the aortic position because it would occlude both coronary artery ostia. A possible solution to this problem is to trim down the wall of the root as it is done in the dissection of aortic homografts prior to their subcoronary surgical insertion. The inflow myocardial orifice would be sutured to the stent followed by the suture of the scalloped aortic wall remnants. Besides the problem of tissue bulk, this technique demands very careful orientation of the valve commissures when inserted to avoid impinging the coronary orifices. This well-recognized surgical problem, always present during the subcoronary implantation of a stentless valve, is magnified when the valve is inserted percutaneously under radiographic or echocardiographic surveillance.

The system for the percutaneous implantation of the sigmoid valve of the present invention is entirely original and far superior to the prior art for the following reasons. Because the sigmoid valve consists only of the leaflets, it offers minimal resistance to the blood flow. Contrary to the aortic, pulmonary, and vein roots used in the prior art, this sigmoid valve has no external tubular wall that could interfere with the coronary orifices.

After construction and implantation, the prosthesis of the present invention follows the principle of the reed present in some musical wind instruments. Its inflow orifice is fixed, but the distal (or outflow) orifice is free to move and vibrate due to eddies created by the forward fluid flow. During valve closure, to avoid bending of the valve and backflow, only two or three sutures anchor the outflow orifice to the wall of the vessel. The presence of an inflow and an outflow circular suture ensure that the geometry of the valve is maintained during its attachment within the endovascular stent. The configuration of the present invention is perfectly adapted for percutaneous implantation because only the inflow orifice of the prosthesis needs to be completely sutured to the supporting endovascular stent. Because the leaflets of the present invention are only fixed at the commissures, stagnant areas where fibrin deposition and thrombus formation can occur (and therefore subsequent embolism can develop) are not found. In alternate preferred embodiments (see FIGS. 7 and 8) of the present invention, the single endovascular stent has a single or triple midsection bulge that imitates the sinuses of Valsalva and comes into contact with the vessel wall but that does not interfere with the coronary ostia.

The prosthesis of the present invention has been tested both in vitro and in vivo in our laboratories. Prototypes were tested in a "pulse duplicator," or mock circulation rig, showing that such a simple valve mechanism functioned perfectly well. Further work showed that temporary support of the inflow and outflow orifices of the valve significantly simplified its surgical implantation. Models of such a device were implanted in the aortic position of isolated pig hearts and tested in the mock circulation rig. The function of the valve, in terms of transvalvular gradients and competence, was excellent. These experiments were followed with in vivo testing. The sigmoid valve of the present invention was implanted under cardiopulmonary bypass in the subcoronary position of the aortic valve in six adult sheep. The sheep were euthanized at 3, 7, and 27 days, and 5 months postoperatively. In all cases, the valve was competent, and the single commissural stitches were well healed and anchored.

DESCRIPTION OF THE SPECIFIC EMBODIMENTS

Figure 1A:
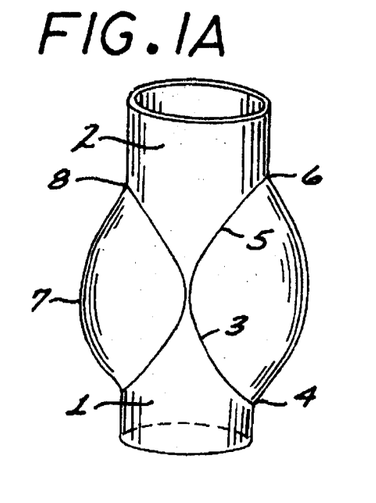
FIG. 1A is a schematic perspective view of a natural mammalian sigmoid valve root.
Figure 1B:
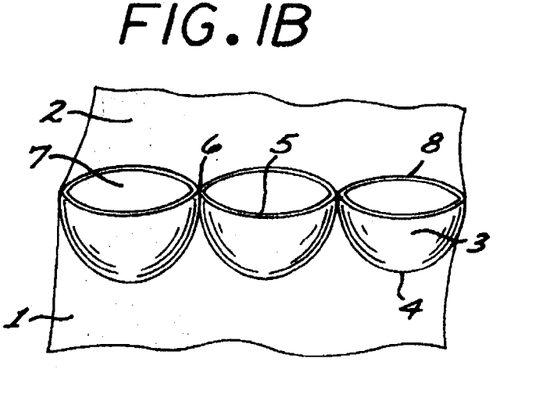
FIG. 1B is a schematic perspective view of the valve root of FIG. 1A that has been partially opened to show its natural components.

Referring now to the drawing figures, FIGS. 1A and 1B are sketches of the basic anatomic structure of a sigmoid valve, such as the aortic valve, pulmonary valve, or the valves present in peripheral veins. All of them are substantially a conduit or root with inflow 1 and outflow 2 orifices separated by three leaflets or cusps 3. FIG. 1A represents a longitudinal section of the root, and FIG. 1B represents a root that has been opened longitudinally to show its major components. The leaflets are attached to the valve annulus 4, which is scalloped, as shown in FIG. 1B. The point where the free edges 5 of the leaflets or cusps 3 come in contact are the commissures 6. Opposite each leaflet, the vessel wall has three bulges or Sinuses of Valsalva 7. The distal (or outflow) limit of the sinuses of Valsalva 7 is the sinotubular junction 8.

Figure 2:
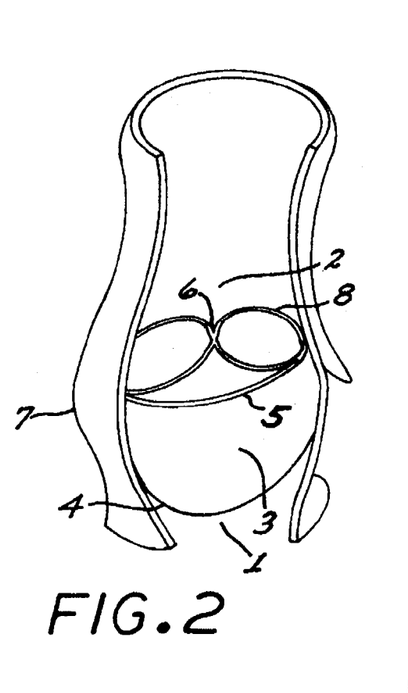
FIG. 2 is a schematic perspective view of a partially opened aortic root.

These structures are depicted closer to reality in FIG. 2, which represents an aortic valve root through an opened aorta. The anatomic landmarks, namely inflow orifice 1, outflow orifice 2, leaflets or cusps 3, base or annulus 4, free edge 5, commissures 6, sinuses of Valsalva 7, and sinotubular junction 8 are essential to be taken into consideration when manufacturing the valve prosthesis of the present invention.

Figure 3:
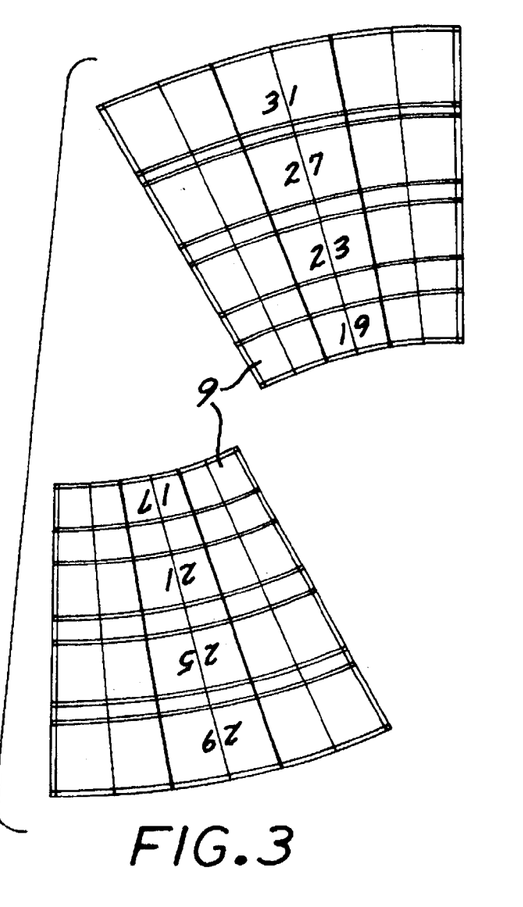
FIG. 3 is a top view of the preferred embodiments of templates that are used to construct the valve of the present invention.

The top view of FIG. 3 shows the dimensions of the flat templates 9 used for the construction of the sigmoid valve of the present invention from a substantially flat, rectangular piece of biocompatible polymer or biologic membrane. Eight different sizes are represented in a 1:1 scale. The numbers correspond to the diameter of the inflow orifice of the valve after it is constructed. These templates can be made of rigid plastic (preferably translucent) or metal. After the diseased native valve has been completely removed, the diameter of the patient's valve annulus is measured with standard sizers well known in the art. The new sigmoid valve is constructed according to this diameter. A template 9 of the corresponding size is selected. FIG. 3 shows the templates 9 for the construction of sigmoid valves of the present invention with inflow diameters of 17, 19, 21, 23, 25, 27, 29, and 31 mm. The number embossed in the template 9 indicates the size of valve prosthesis that will result from using that particular template.

Figure 4:
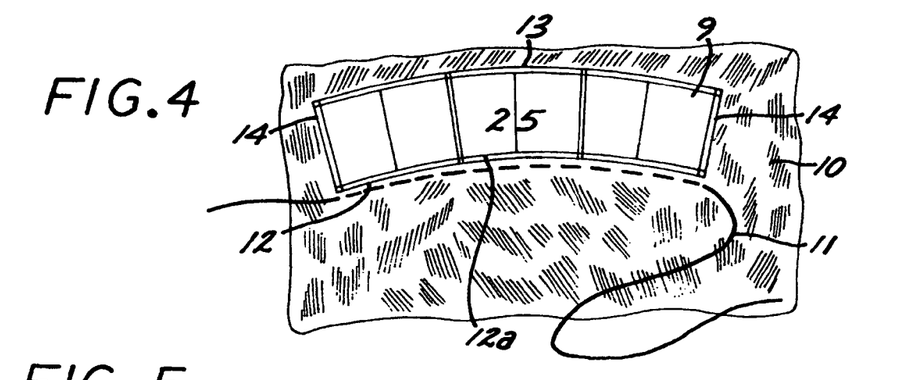
FIG. 4 is a top view showing the template placed on a flat biologic or synthetic membrane in the process of constructing the valve of the present invention.

FIG. 4 shows how the template 9 is used to trim the biologic membrane 10 to the appropriate size and shape. In this case, a 25 mm template 9 is used that corresponds to a valve with an inflow orifice diameter of 25 mm. The number "25" embossed in the template 9 indicates the diameter of the inflow orifice 1 after the valve is constructed. A rectangular piece of biocompatible polymer or biologic membrane 10 is used for the manufacture of the sigmoid valve of the present invention. In the preferred embodiment, a piece of pericardium of approximately 10×5 cm from the patient or from an animal (such as pig, calf, or horse) is obtained. The pericardium needs to be freed from alveolar tissue and treated according to whether it is autologous, homologous, or heterologous with chemical and physical treatments well known in the art (such as buffered glutaraldehyde). Alternatively, the pericardium can be treated with one of the treatments described in U.S. Pat. No. 6,352,708 or in U.S. Pat. No. 6,277,555B1. The treated pericardium 10 is placed on a flat surface and covered with the template 9. In one of the preferred embodiments, a needle (not shown) carrying 2/0 polypropylene suture or wire 11 is then passed through the pericardium parallel and a few millimeters from the smaller curvature 12 of the template 9. This suture 11 will become the first or inflow encircling support 17 of the prosthesis of the present invention. The pericardium is then trimmed with tools (not shown), such as scissors, surgical scalpel, or a cutting die, following the shape of the template 9 but also including the suture 11. A trapezoidal piece of pericardium with a base 12a, a top 13, and two lateral sides 14 is then available for the construction of the sigmoid valve 15.

Figure 5:
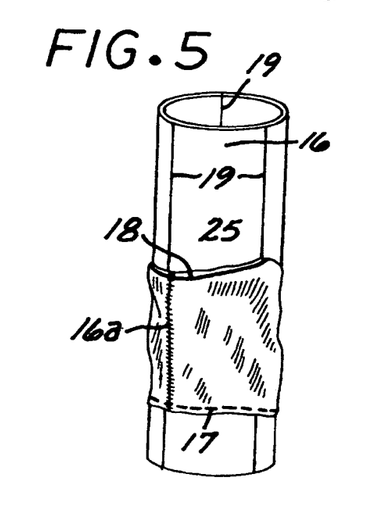
FIG. 5 is a perspective view showing another step in the process of constructing the valve of the present invention.

FIG. 5 demonstrates the steps to be followed for the construction of the sigmoid valve 15 with the trimmed flat piece of pericardium 10. The pericardium is wrapped around a mandrel 16 corresponding to the valve diameter (e.g., in this case with a diameter of 25 mm). The mandrel 16 can be a simple cylinder or, in the preferred embodiment, a truncated cone of slightly smaller dimensions than the intended valve. The two lateral sides 14 of the pericardial trapezoid are then joined with a running suture of thin, biocompatible filament 16a, such as 4/0 to 6/0 polypropylene. A truncated cone results with proximal (or inflow) and distal (or outflow) orifices. The previously placed thicker (2/0 polypropylene) suture 11 is then tied over the truncated cone to form the flexible first or inflow circular support 17. Another similar 2/0 suture is placed around the mandrel 16 and tied close to, but not through, the outflow orifice of the truncated cone. This suture forms the flexible second or outflow circular support 18 of the sigmoid valve 15. Three equidistant points, or commissures, of the truncated cone are selected. These points are sutured to three equidistant points of the second or outflow circular support 18. The ends of the first and second circular supports 17 and 18 can be joined with a surgical knot, if performed during surgery, or with methods such as crimping, gluing, or other methods well known in the art. The mandrel 16 has three longitudinal marks 19 situated at 120 degrees apart to orient the placement of the commissural stitches in the outflow orifice of the sigmoid valve 15. After the just described steps or operations are completed, the valve 15 is removed from the mandrel 16.

Figure 6:
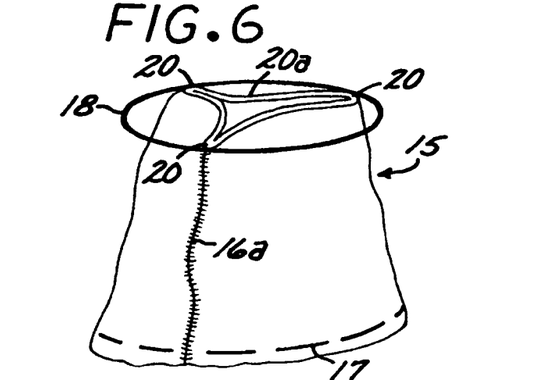
FIG. 6 is a perspective view of the valve of the present invention.

FIG. 6 is a perspective view of the final aspect of the sigmoid valve 15 of the present invention. The pericardial truncated cone is formed by the suture 16a of the lateral sides of the formerly flat trapezoidal piece of pericardium 10. The first or inflow circular support 17 holds the whole circumference of the valve inflow orifice 1. The outflow orifice 2 of the valve 15 is attached to the second outflow circular support 18 at only three equidistant points 20 separated by 120 degrees (marked 19 on the mandrel 16 in FIG. 5). Although three commissures 20 are attached to the second or outflow circular support 18, the rest of the pericardial outflow orifice of the sigmoid valve is free and forms the free edges 20a of the three leaflets 3.

FIG. 7A is a perspective side view of that embodiment of the sigmoid valve 15 which per se is shown in FIGS. 11A and 11B. This valve 15 is placed within a straight endovascular stent 22. In FIG. 7A, the first and second circular supports 17 and 18, corresponding to the inflow 1 and outflow 2 orifices of the sigmoid valve 15, are connected by three equidistant sutures 23 that define and maintain a maximum distance between them. These sutures 23 are placed at 120 degrees relative to each other and correspond with the three commissural points of the outflow orifice 2 of the sigmoid valve 15. The length of these sutures 23 corresponds to the height of the sigmoid valve 15. As shown in FIG. 7A, the first or inflow circular support 17 has been sutured to the endovascular stent 22, but the second or outflow circular support 18 has not been sutured yet. Open arrows 24 show where the second or outflow circular support 18 is going to be sutured into the endovascular stent 22. This suture will outwardly expand the endovascular stent 22, resulting in a bulge 25 or sinus of Valsalva, which is shown in FIG. 7B. The black arrows 26 indicate that the height of the sigmoid valve 15 is maintained constant because of the presence of the connecting sutures 23. In FIG. 7B, for simplicity, the final shape of the endovascular stent 22 with the midsection bulge 25 or sinus of Valsalva is shown without showing the sigmoid valve 15.

FIG. 8A is a perspective side view of the sigmoid valve 15 placed within an endovascular stent 22 designed with a wider midsection or bulge 25 that corresponds to the sinuses of Valsalva. The inflow and outflow circular supports 17 and 18 of the sigmoid valve 15 have been sutured to the endovascular stent 22 at the levels where the two extremities of the bulge 25 correspond to the sinuses of Valsalva. More specifically, the second or outflow circular support 18 of the sigmoid valve 15 has been sutured to the endovascular stent 22 beyond the bulge 25 corresponding to the sinus of Valsalva, and only at three equidistant points.

There are multiple methods of creating a stent with bulges. In the embodiment of FIG. 7A, the endovascular stent is straight. Suturing the outflow portion of the valve into the endovascular stent beyond the length of the valve induces a bulge in the stent. Another method is shown in the embodiment of FIG. 8A, where the endovascular stent already has pre-formed single or triple bulges. During implantation, guided by a catheter, the endovascular stent 22 is deployed in the appropriate location. This is the presently preferred embodiment for the percutaneous placement of the sigmoid valve 15 in pulmonary and peripheral vein locations of mammals, including humans. FIG. 8B shows the inflow view, and FIG. 8C shows the outflow view of the sigmoid valve 15 within the endovascular stent 22. In FIG. 8B, the sigmoid valve 15 is in the open position; therefore, only the bulge 25 corresponding to the sinus of Valsalva and the first or inflow circular support 17 sutured to the endovascular stent 22 are shown. In FIG. 8C, the sigmoid valve 15 is shown in the semiclosed position, showing that the second or outflow circular support 18 of the sigmoid valve 15 is sutured to the endovascular stent 22.

FIG. 9 is a diagrammatic perspective view of the sigmoid valve 15 already implanted in a coronary artery 26a. In this preferred embodiment, self-expanding or balloon-expandable endovascular stents 27 and 28 are sutured to the inflow and outflow circular supports 17 and 18 of the sigmoid valve 15. Such self-expanding or balloon-expandable endovascular stents are well known in interventional cardiology and are commercially available. After implantation, the self-expanding or balloon-deployed endovascular stents 27 and 28 fix the sigmoid valve 15 in the correct position (i.e., in the inflow and outflow tract of the patient's aortic or pulmonary root, or in a vein). The sinuses of Valsalva 7 and coronary arteries' ostia 29 are free and at a distance from the sigmoid valve 15.

Figure 10:
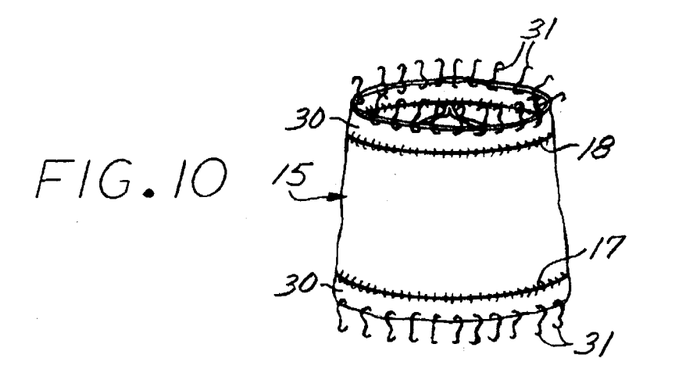
FIG. 10 is a perspective of the sigmoid valve of the present invention prepared for percutaneous implantation but before it is placed in an endovascular stent.

FIG. 10 is a perspective view of the sigmoid valve 15 of the present invention modified in a still different manner for percutaneous implantation. In this embodiment, a short sleeve 30 of approximately 1 cm of DACRON™ conduit of a diameter similar to the inflow orifice of the sigmoid valve 15 is sutured to the inflow orifice 1 of the sigmoid valve 15. A similar sleeve 30 of DACRON™ of diameter similar to the outflow orifice 2 is sutured directly to the second or outflow circular support 18, because the pericardium of the outflow orifice of the sigmoid valve 15 is held to the outflow circular support 18 at only three points (corresponding to the valve commissures). The two DACRON™ sleeves 30 incorporate a series of hooks 31 similar to those used for the percutaneous anchoring of intravascular conduits, which is well known in the prior art. The hooks of this embodiment are implanted directly into the patient's vessel wall. No endovascular stent is used.

FIGS. 11A and 11B show in detail that embodiment of the valve 15 of the present invention which is incorporated in the embodiment of the system shown in FIG. 7A. The three vertical sutures or arms 23 made of a thin wire or flexible plastic material interconnect the first or inflow 17 and second or outflow 18 circular supports at the level corresponding to the commissures 6 of the tissue valve 15. The connecting sutures or arms 23 are affixed to the circular supports 17 and 18 by any suitable method known in the art, such as suturing. The object of the connecting arms 40 is to facilitate the correct orientation and distance between the inflow 1 and outflow orifices 2 of the tissue valve 15 after the inflow orifice 1 has been sutured in place. Twisting and over- or understretching of the valve 15 is therefore avoided.

Figure 12:
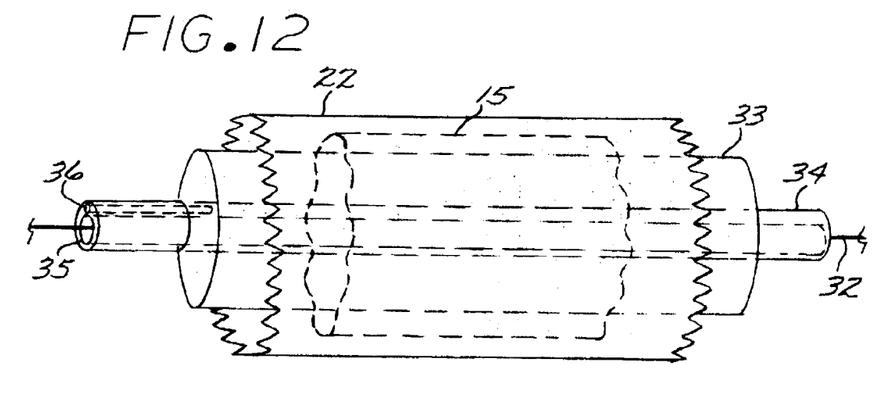
FIG. 12 is a schematic perspective view of a delivery system for delivery and deployment of the sigmoid valve of the present invention.

There are several known methods and systems in the art for percutaneous delivery and deployment of a prosthetic valve such as the sigmoid valve of the present invention. FIG. 12 illustrates one such delivery system. This delivery system is used when the endovascular stent 22 is not self-expanding, and must be inflated with a balloon. The system includes a thin steerable guide wire 32 which is introduced percutaneously into a vein or artery (not shown) with the well known Seldinger technique. Because the Seldinger technique is known in the art, it does not need to be described here. This guide wire 32 is then pushed along the patient's blood vessel to the desired position. After the guide wire 32 is across the native valve which is intended to be replaced, the guide wire 32 is rested. In case of cardiac valve replacement it rests in the left ventricle (not shown). An inflatable balloon 33 is placed within the endovascular stent 22 to which the novel valve 15 of the present invention is attached, as described above. A catheter 34 is placed on to the guide wire 32. Better stated, the catheter 34 has a central coaxial hole 35 into which the guide wire 32 is placed. The catheter 34 has another coaxial but not necessarily centrally located hole 36 which extends only as far as the balloon 33 is to be pushed along the wire 32. The purpose of the hole 36 is to allow introduction of liquid, such as water or saline, to inflate the balloon 33. Although for the sake of illustration FIG. 12 does not show the stent 22, valve 15 and balloon 33 in a collapsed state, these items are actually collapsed and the balloon 33 is deflated over the catheter 34, so that the stent/valve/balloon combination is advanced over the guide wire 32 until it crosses the native valve (such as the aortic valve) which is intended to be replaced by the prosthetic valve 15. The balloon 33 is then expanded by introduction of a liquid, such as water or saline through the hole 36 in the catheter 34 until it pushes the endovascular stent 22 into the wall of the native valve or vessel (such as the aortic valve and aorta) and causes any additional attachment means, such as the hooks 31 (see FIG. 10) sharp points (not shown) or other state-of-the-art means to fix the stent 22 into the vessel wall. Then the balloon 33 is deflated by suctioning out the liquid, and the stent 22 and the attached prosthetic valve 15 of the invention are left in place. By this technique, the original native valve's leaflets are pushed out of the way and trapped outside the stent 22. The guide wire 32, balloon 33 and catheter 34 per se are well known in the art, and need not be described here in further detail.

Figure 13:
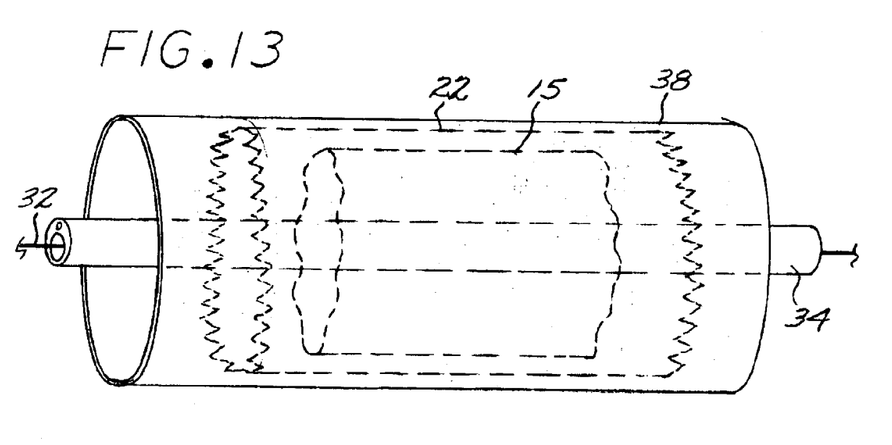
FIG. 13 is a schematic perspective view of another delivery system for delivery and deployment of the sigmoid valve of the present invention.

FIG. 13 illustrates another delivery system that is used when the endovascular stent 22 to which the valve 15 of the invention is mounted, is self-expanding and need not be expanded with a balloon. As noted above, self-expanding stents are known and available in the state-of-the-art. Although a self-expanding stent does not need to be expanded with an inflatable balloon, precisely because it is self expanding it must be restrained from expansion while it is being pushed along the patient's blood vessel to its desired destination. Thus, in this system of delivery the catheter 34 is on the guide wire 32, and the self-expanding endovascular stent 22 with the attached valve 15 of the invention is placed on the catheter 34 in a collapsed state. Again, as in FIG. 12 in FIG. 13 also for the sake of better illustration the valve and stent combination is not shown collapsed, although in actual practice these items are collapsed. This delivery system may also be used with the inclusion of an inflatable balloon (not shown in FIG. 13) when a "bare" stent 22 of the technique described in connection with FIG. 12 may not be able to traverse a heavily calcified artery.

As shown in FIG. 13, the collapsed endovascular stent 22 and attached valve 15 are restrained from expansion by a second delivery catheter 38 that is of a larger diameter than the catheter 34 on the guide wire 32 that carries the collapsed valve 15 and stent 22 (self-expanding or balloon expandable). When the stent 22 is self-expanding then removal of the delivery catheter 38 permits the stent 22 to deploy spontaneously within the patient's vessel. When a non--self-expanding stent 22 is used, the catheter 34 that carries the valve 15 and stent 22 is centrally placed over a collapsed balloon 33 (not shown in FIG. 13). Inflation of the balloon 33 will expand the stent 22 and valve 15. After the valve 15 and stent 22 are deployed, the delivery catheter 38 and guide wire 32 are pulled from the blood vessel, and the hole in the vessel is closed surgically or with one of the percutaneous closure devices commercially available.

In some cases, the overall cross-section of the delivery catheter 38 is such that the patient's peripheral artery must be dissected with a small surgical incision. Alternatively, one can use the venous system, which is much larger than the arteries. To do this would require the standard means of crossing the interatrial septum and placing the wire retrograde through the aortic valve and out the femoral artery. One can then introduce the "bare" stent device of FIG. 12, or the delivery catheter 38 through the vein without artery surgery if the device is larger than the artery. This is also the method to place a valve in the right side of the heart (such as the pulmonary valve).

In accordance with the present invention, the valve and it implantation system can be constructed under sterile conditions at the time of the intervention by a physician, using either a flat membrane or an artery or vein of animal origin. In this case, the constructed valve of the present invention is affixed to commercially available, standard endovascular stent or stents of the appropriate diameter(s), as described above. Then the valve and stent are wrapped around a balloon catheter and implanted into the patient with the use of a delivery catheter.

However, in the majority of cases, the operating surgeon is likely to use a combination of a valve with the endovascular stent or stents already affixed that has been constructed in a dedicated environment where one or more the embodiments described above are manufactured commercially.

What is claimed is:

1. A combination of an endovascular stent with an intravascular multi-leaflet, one-way valve to serve as a prosthesis for diseased native valve of a mammal, the combination being adapted for percutaneous delivery, and comprising:
   (1) a valve including a tubular member formed of one of a naturally occurring tubular body channel and of a membrane, the membrane being selected from a group of materials consisting of biocompatible polymer and biologic flat membrane, said membrane formed into the tubular member and configured as a truncated cone, the tubular member having an inflow orifice and an outflow orifice, the leaflets forming the outflow orifice and forming a plurality of comissures;
   a first encircling support consisting essentially of material selected from the group consisting of thin metal wire, thin plastic ring, or suture filament, said first encircling support being affixed in a substantially circular fashion around the tubular member in proximity of the inflow orifice, and
   a second encircling support consisting essentially of material selected from the group consisting of thin metal wire, thin plastic ring, or suture filament, said second encircling support being affixed solely at the locations of the comissures to form a circle around the tubular member in proximity of the outflow orifice;
   (2) an endovascular stent larger in diameter than the valve, the valve being contained in the endovascular stent and attached to the endovascular stent by affixing the inflow orifice of the valve to the endovasular stent and by affixing the second encircling support to the endovascular stent, the endovascular stent including an outwardly extended bulge in an area where the valve is attached within the endovacular stent, said bulge corresponding to the sinuses of Valsalva.

2. A combination in accordance with claim 1 wherein the bulge of the endovascular stent comprises material of the endovascular stent that is longer than the length of the valve and that is held as the bulge by sutures placed at the inflow and outflow orifices of the valve.

3. A combination in accordance with claim 1 where the endovascular stent is collapsible and self-expandable.

4. A combination in accordance with claim 1 where the endovascular stent is collapsible and balloon inflatable.

5. A combination in accordance with claim 1 wherein the valve is a tri-leaflet valve.

6. A combination in accordance with claim 1 wherein the valve is a bi-leaflet valve.

7. A combination in accordance with claim 1 where the valve is attached to the endovascular stent by sutures.

8. A combination in accordance with claim 1 where the valve further comprises a plurality of members interconnecting the first and second circular supports, the length of the interconnecting members determining the maximum height of the valve.

* * * * *

UNITED STATES PATENT AND TRADEMARK OFFICE
CERTIFICATE OF CORRECTION

PATENT NO. : 7,125,418 B2 Page 1 of 1
APPLICATION NO. : 10/411797
DATED : October 24, 2006
INVENTOR(S) : Duran It is certified that error appears in the above-identified patent and that said Letters Patent is hereby corrected as shown below:

On title page Item [75] Delete, "Inventor Mark Sanz" of the patent, first column, line 4 for inventors (Request to Amend Inventorship, dated March 7, 2006 and Corrected Filing Receipt, mailed on August 8, 2006, line for Applicant(s)) "Mark Sanz, Missoula Mt (US)" should be deleted.

Signed and Sealed this

Sixth Day of March, 2007

JON W. DUDAS
*Director of the United States Patent and Trademark Office*